(12) United States Patent
Symons

(10) Patent No.: US 6,503,638 B1
(45) Date of Patent: Jan. 7, 2003

(54) IMPREGNATION OF A LIGNOCELLULOSIC MATERIAL

(75) Inventor: Michael Windsor Symons, Monument (ZA)

(73) Assignee: Windsor Technologies Limited, Nassau (BS)

( * ) Notice: Subject to any disclaimer, the term of this patent is extended or adjusted under 35 U.S.C. 154(b) by 0 days.

(21) Appl. No.: 09/646,418

(22) PCT Filed: Mar. 18, 1999

(86) PCT No.: PCT/GB99/00841

§ 371 (c)(1),
(2), (4) Date: Oct. 27, 2000

(87) PCT Pub. No.: WO99/47319

PCT Pub. Date: Sep. 23, 1999

(30) Foreign Application Priority Data

Mar. 18, 1998 (ZA) .............................................. 98/2276

(51) Int. Cl.⁷ ............................ B32B 27/42; B27K 3/46; B27K 3/50
(52) U.S. Cl. ..................... 428/526; 428/524; 428/528; 428/530; 428/541; 525/480; 525/491
(58) Field of Search ................................ 428/526, 524, 428/528, 530, 541; 525/480, 491; 528/129, 137, 142; 568/799, 752, 780

(56) References Cited

U.S. PATENT DOCUMENTS

| | | | | |
|---|---|---|---|---|
| 3,843,576 A | * | 10/1974 | Parkinson | 524/510 |
| 3,946,137 A | * | 3/1976 | Power et al. | 428/452 |
| 3,973,971 A | * | 8/1976 | Greco et al. | 106/15 R |
| 4,065,273 A | * | 12/1977 | Rudolph | 55/50 |
| 4,201,851 A | * | 5/1980 | Chen | 528/1 |
| 4,433,031 A | * | 2/1984 | Allen, Sr. | 428/541 |
| 5,820,967 A | * | 10/1998 | Gadkaree | 428/116 |

FOREIGN PATENT DOCUMENTS

| | | |
|---|---|---|
| AT | 514 897 | 3/1981 |
| FR | 631 594 | 12/1927 |
| GB | 1 218 348 | 1/1971 |
| JP | 55116792 | * 9/1980 |

OTHER PUBLICATIONS

Database WPI, Section Ch, Week 8348, Derwent Publications Ltd. Class A21, AN 83–831862, XP002106200 & SU 994 262, Feb. 1983.
Database WPI, Section Ch Week 9145, Derwent Publications Ltd., Class A21, An 91–331078, XP002106201, & SU 1630889, Feb. 28, 1991.

* cited by examiner

Primary Examiner—Shrive P. Beck
Assistant Examiner—Elena Tsoy
(74) Attorney, Agent, or Firm—Pillsbury Winthrop LLP

(57) ABSTRACT

A composition for impregnation of a lignocellulosic material such as wood or wood particles, comprises a high boiling point tar acid or a pitch derived from coal; a solvent for the tar acid or pitch selected from a low carbon alcohol, an aceotrope of a low carbon alcohol and another solvent, and a mixture of a lower carbon alcohol and water; a phenol formaldehyde resole resin; an acid catalyst for the phenol formaldehyde resole resin; and preferably a formaldehyde donor or a precursor thereof. There is also disclosed a method of preparing a finished product from a lignocellulosic material by using the impregnating composition.

22 Claims, No Drawings

IMPREGNATION OF A LIGNOCELLULOSIC MATERIAL

This application is the national phase of international application PCT/GB99/00841 filed Mar. 18, 1999 which designated the U.S.

BACKGROUND OF THE INVENTION

This invention relates to a composition for impregnation of a lignocellulosic material, and to a method of preparing a finished product from a lignocellulosic material which has been so impregnated.

It is well known to preserve timber by impregnating preservatives in a pressure cylinder, usually with a vacuum/pressure, vacuum/vacuum, pressure/pressure or pressure/pressure/vacuum cycle. Examples of suitable preservatives are the copper chrome arsenates in water, creosotes, and MDIs with or without anhydrides in non aqueous solvents.

Desirable properties to be imposed upon wood are resistance to water ingress, resistance to the movement of water in the material by capillarity, preventing attack of the lignocellulosic material by micro organisms, particularly fungi or insects such as termites, stabilising the wood dimensionally, improving its mechanical properties and possibly also improving its appearance. Very few of the known impregnation technologies accomplish all of these objectives.

SUMMARY OF THE INVENTION

According to a first aspect of the invention, there is provided a composition for impregnation of a lignocellulosic material, which composition comprises:
  (a) a high boiling point tar acid or a pitch derived from coal;
  (b) a solvent for component (a) selected from the group consisting of a low carbon alcohol, an azeotrope of a low carbon alcohol and another solvent, and a mixture of a lower carbon alcohol and water;
  (c) a phenol formaldehyde resole resin;
  (d) optionally an acid catalyst for the phenol formaldehyde resole resin; and
  (e) optionally a formaldehyde donor or a precursor of formaldehyde.

By a lignocellulosic material there is meant any plant material emanating from the photosynthetic phenomenon.

The lignocellulosic material may, for example, be chosen from wood in sawn, sliced, peeled or veneer form; plywood; paper; woven strands; fibres, particles, flakes or chips of wood or agricultural products; or the like.

A preferred impregnating composition of the invention comprises:
  (a) a high boiling point tar acid or a pitch derived from coal in an amount of from 2% to 60% inclusive by mass, more preferably from 8% to 15% inclusive by mass of the combined mass of components (a), (b) and (c);
  (b) a solvent selected from the group consisting of a low carbon alcohol, e.g. methanol, ethanol, propanol or butanol, preferably methanol; an azeotrope of a low carbon alcohol and another solvent, and a mixture of a low carbon alcohol and water; in an amount of from 50% to 97% inclusive by mass, more preferably from 77% to 90% inclusive by mass of the combined mass of components (a), (b) and (c);
  (c) a phenol formaldehyde resole resin in an amount of from 1% to 30% inclusive by mass, more preferably from 2% to 8% inclusive by mass of the combined mass of components (a), (b) and (c);
  (d) an acid catalyst for the phenol formaldehyde resole resin in an amount of from 1% to 15% inclusive by mass, more preferably from 4% to 6% inclusive by mass of the resin; and
  (e) a formaldehyde donor or a precursor of formaldehyde, such as hexamethylene tetramine, in an amount of from 1% to 15% inclusive by mass, more preferably from 8% to 12% inclusive by mass of the mass of the high boiling point tar acid or the pitch.

The solvent, component (b), also acts as an extending liquid for the phenol formaldehyde resole resin.

The impregnating composition may also contain other components such as an antioxidant and a deodoriser, both of which should be miscible or soluble in the extending liquid.

A preferred level of impregnation for upgrading wood for exterior exposure is, for example, 2% by mass of resin with 10% by mass of pitch on the mass of the dry wood.

According to a second aspect of the invention, there is provided a method of preparing a finished product from a lignocellulosic material, including the steps of:
  (i) impregnating the lignocellulosic material with an impregnating composition as set out above;
  (ii) removing the solvent from the product of step (i), optionally with recovery thereof for reuse; and
  (iii) subjecting the product of step (ii) to suitable conditions of temperature and optionally of pressure to polymerise or to set the resin, to form the finished product.

Step (i) of the method of the invention may be carried out by immersing the lignocellulosic material in the impregnating composition, or by impregnating the lignocellulosic material with the impregnating composition under suitable conditions of vacuum and pressure.

In step (ii) of the method of the invention, the solvent may be removed from the product of step (i) in any suitable way.

In step (iii) of the method of the invention, the product of step (ii) may be subjected simply to an elevated temperature, for example, a temperature exceeding 90° C., to allow the resin to polymerise or set. Alternatively, when the lignocellulosic material is in particulate form, the product of step (ii) may be subjected to suitable conditions of temperature, e.g. a temperature exceeding 90° C., and pressure, for example, between the platens of a press, to allow the resin to polymerise or set and thus to adhere the particles to one another to form the finished product.

According to a third aspect of the invention, there is provided a finished product comprising a lignocellulosic material which has been impregnated with an impregnating composition as set out above, the impregnated lignocellulosic material having been subjected to suitable conditions of temperature and optionally of pressure to polymerise or to set the resin, to form the finished product.

DESCRIPTION OF EMBODIMENTS

The crux of the invention is a composition for impregnation of a lignocellulosic material which comprises a high boiling point tar acid or a pitch derived from coal, a solvent therefor, and a suitable compatible binder to bind the tar acid or the pitch in the lignocellulosic material.

The first component of the impregnating composition of the invention is the high boiling point tar acid or the pitch derived from coal, particularly derived from the water stream in the distillation classification of coal.

During the distillation of coal, there is produced gas, tars and a water stream containing high boiling point tar acids and pitches. It is these latter products which are useful in the impregnating composition of the invention.

It is important that the high boiling point tar acid or pitch is partially or completely dissolved in the solvent in order that impregnation of the lignocellulosic material occurs.

An example of a suitable tar acid is Merisol XHBTA produced by Merichem-Sasol RSA (Pty) Limited, which product has a boiling point in the range 210° C. to 300° C. at atmospheric pressure, and a density of 1,03. This product is only sparingly soluble in water, but readily soluble in the low carbon alcohols and acetates. It has a composition of 20% to 30% ethyl phenols, 40% to 60% xylenols, and 15% to 25% high boiling point tar acids.

A further suitable material is a phenosolven pitch of a density in the range 1.01 to 1.06, and with a composition of 12% higher boiling point tar acids, 12% N cresol. 21.8% M & P cresol, 8% xylenols and the balance being phenols, and which is substantially soluble in methanol.

The function of this component is to impose resistance to water ingress on the lignocellulosic material and to prevent attack of the lignocellulosic material by microorganisms, particularly fungi, or insects, or the like.

The second component of the impregnating composition of the invention is a solvent for the tar acid or the pitch. The solvent may be a low carbon alcohol such as methanol, ethanol, propanol or butanol, preferably methanol; an azeotrope of a low carbon alcohol, preferably methanol and another solvent, i.e. methyl acetate 80%/methanol 19% with a boiling point of 54° C. or an azeotrope with ethylacetate or acetone; or a mixture of a low carbon alcohol, preferably methanol, and water.

The solvent also acts as an extending liquid for the phenol formaldehyde resole resin.

Thus the function of the solvent or extending liquid is also to prevent resin polymerisation in the impregnating composition and in the impregnated lignocellulosic material until the solvent or extending liquid has been removed.

In addition, the solvent or extending liquid serves to control the viscosity of the impregnating composition. The solvent or extending liquid also allows control of the impregnation composition solids that are left in the impregnated material, which is important commercially and which allows control of the final properties of the finished product.

The third component of the impregnating composition is a phenol formaldehyde resole resin. The phenol formaldehyde resole resin may be one that is a water borne and water dilutable thermosetting phenol formaldehyde resin, examples being Schenectady International SG 3100, HRJ-4173 with solids percentages between 65% and 82% and Code J 2018 L by Blagden-Cellubond Limited of the UK. The resin may be produced at high solids content in a water miscible solvent, making the resin water dilutable and allowing water compatibility of the less polar or high molecular weight phenolic resins. A true solution is preferred to a dispersion or emulsion in order to achieve true penetration and fibre wetting of the lignocellulosic material and avoiding surface blocking and accumulation on impregnation.

The function of the phenol formaldehyde resole resin is to contribute to the hardness and dimensional stability of the finished product, to improve the mechanical properties thereof, and to bind the high boiling point tar acid or the pitch into the matrix or cellular structure of the lignocellulosic material.

The fourth optional component of the impregnating composition of the invention is an acid catalyst for the phenol formaldehyde resole resin. Examples of suitable catalysts are Phencat 10 and Phencat 15 by Blagden-Cellubond Limited, and catalysts based on sulphonic acid.

The function of the acid catalyst is to promote the polymerisation of the phenol formaldehyde resole resin once the solvent or extending liquid has been removed.

The resin may however polymerise simply with the application of heat.

The fifth optional component of the impregnating composition of the invention is a formaldehyde donor or a precursor of formaldehyde, such as for example hexamethylene tetramine, methylene glycol, trimethylene glycol and paraformaldehyde.

Thus, for example, hexamethylene tetramine serves as a formaldehyde donor to facilitate the polymerisation of the phenol formaldehyde resole resin and reactive elements in the high boiling point tar acids and pitches, and promote the consolidation of these compounds to the chemical makeup of the phenol formaldehyde resole resin.

The second aspect of the invention is a method of preparing a finished product from a lignocellulosic material.

The first step of the method is to impregnate the lignocellulosic material with an impregnating composition as set out above.

The impregnation may take place by immersion or by impregnation under pressure. Various examples of methods of impregnation are set out below:

1A Placing the lignocellulosic material in a pressure cylinder; subjecting it to a vacuum, generally to the lowest possible pressure consistent with its moisture percentage and for periods of time, typically of 5 to 25 minutes; flooding the cylinder with the impregnating composition; subjecting the cylinder to a positive pressure in the range of 1 to 25 bar, but more generally in the range of 2 to 8 bar, for a period of time such as 10 to 40 minutes; removing the impregnating composition from the cylinder and withdrawing the material.

1B Placing the lignocellulosic material in a pressure cylinder; subjecting it to a vacuum, the level of which is governed by the moisture percentage in the lignocellulosic material, the length of time under vacuum being from 5 to 30 minutes; flooding the cylinder with the impregnating composition; allowing a dwell time for penetration for up to 40 minutes and then removing the impregnating composition.

1C. Where limited penetration of the impregnating composition into the lignocellulosic material is required, placing the material in a pressure cylinder and subjecting it to a positive gas pressure, the pressure being between 0,5 and 3 bar, for 5 to 20 minutes; flooding the cylinder while still under pressure with the impregnating composition; maintaining the pressure in the cylinder during this operation at a constant level; once full, subjecting the contents of the cylinder to a positive pressure exceeding the first pressure and being in the range of from 1,5 bar to 8 bar, the differential between the first and second pressures controlling the depth of penetration into the lignocellulosic material; removing the impregnating composition and then subjecting the lignocellulosic material to a vacuum for period of from 5 to 20 minutes in order to release the internal air pressure in the lignocellulosic material, thus minimising subsequent kick back or exudation of the composition from the impregnated material.

1D Subjecting the lignocellulosic material to any of the processes 1A to 1C above, and then repeating the process particularly having subjected the impregnated material between treatments to a vacuum in order to remove as much of the solvent between cycles as is possible. This step increases the level of chemical modifiers left in the lignocellulosic material.

1E Where the lignocellulosic material is in thin sheet form such as paper in weights of from 100 to 600 g/m², being either virgin kraft or recycled paper chip or kraft, or woven hessian and the like or in chip or particle form, or thin veneer, immersing the material in the impregnating composition.

1F Where the lignocellulosic material is in particle form, placing it in a mixer; adding the impregnating composition on a pre-determined weight basis; mixing rapidly, generally not exceeding 3 minutes in time; and removing the impregnated particles from the mixer.

The second step of the method of the invention is to remove the solvent from the product of step (i), optionally with recovery thereof for reuse.

The recovery of the solvent from the treated material may be carried out by placing it in a suitable kiln or drier and subjecting it to gas movement, preferably air, at a temperature propagating the most rapid and economical evaporation of the solvent from the treated material, until this process is complete, followed by escalating temperature to ensure the completion of the chemical reactions required.

The third step of the method of the invention is to subject the product of step (ii) to suitable conditions of temperature and pressure to polymerise the phenol formaldehyde resole resin, to form the finished product.

For example, when the lignocellulosic material is in sheet form, then the material may be subjected to conditions of elevated temperature, preferably at a level exceeding 90° C., to induce polymerisation of the resin.

Alternatively, when the lignocellulosic material is in particulate form, the particles may be subjected to a combination of elevated temperature, preferably exceeding 90° C., and pressure, for example, between the platens of a press, to induce the resin to polymerise and to form the finished product. In this way, chipboard, oriented strand board, medium density fibre board, flake board and the like can be manufactured.

Examples of the invention will now be given.

Example 1

100 kg of phenol formaldehyde resole resin Code J 2018 L by Poly Resin Products South Africa is added to 600 kg of methanol. 60 kg each of phenosolven pitch from Sasol Tar Division of Sasol Chemicals, South Africa, and 60 kg of XHBTA Higher boiling point tar acid by Merichem-Sasol RSA (Pty) Ltd, are blended. There is added to this blend 8 kg of hexamethylene tetramine and this mix is added to and dissolved in the resin/methanol composition. Finally, 9 kg of acid catalyst Phencat 10 by PRP Resins South Africa is added. Lengths of pine being 1 m long, 22 mm thick and 150 mm wide, are placed in a pressure cylinder and subjected to a vacuum for 15 minutes. A final pressure of 15 kPa is achieved. The impregnating composition is now introduced into the cylinder and subjected to a pressure of 6 bar for 25 minutes. The average uptake of the impregnating composition per dry kg of pine is in the range of 875 g to 1.1 kg. The charge is removed from the impregnating cylinder and placed in an extractor kiln where the methanol is removed, using a circulating closed loop with air velocity of 5 meters per second at a temperature of 40° C. Once the methanol has been removed the temperature is raised progressively to 110° C. until the chemical reactions in the material have gone to completion. The resulting pine has improved resistance to water penetration and movement in the material by capillarity. It is disinfected to the point of being proof to either fungi or termites and the hardness of the material has been increased from typically 2500 Newtons on the Janka Ball Test to 5 500 Newtons. The resulting wood is fit for exterior ground contact applications.

Example 2

A mixture comprising of one part of J 2018 L phenol formaldehyde resole resin, four parts of a 50% blend between XHBTA high boiling point tar acid and phenosolven pitch from Sasol, 0,4 parts hexamethylene tetramine and 0,75 parts of methanol are blended, and then 0,08 parts of acid catalyst Phencat 10 are added in an in-line mixer and sprayed onto wood particles at the rate of 10% on a mass basis. To the damp wood particles is now added 3% on a mass basis of a phenol formaldehyde novolac resin in finely divided dry powder form V12 Code Cellubond CH 113 by Blagden-Cellubond Ltd. of the UK. The wood chips progress continuously through a drier, removing all of the methanol which is scrubbed from the emitted air. The wood particles are now passed through a forming head which lays down a mat on a moving belt at the rate by mass of 11,5 kg/m². This mat is then pressed between heated press platens at a pressure of 25 kg/cm² making a particle board of a density of 720 kg/m³ and a thickness of 16 mm. The properties of the board are a much increased resistance to water swell on submersion. The composite is proof to attack by termites or fungi and has a much improved internal bond strength.

In the two examples above, the Rideal-Walker coefficient is anticipated to be between 5 and 16. The standard Rideal-Walker (RW) test compares the amount of dilution possible with the test sample to obtain the same bactericidal or fungicidal efficiency as a 1 gram in 100 ml phenol sample. The ratio of the dilution gives the RW coefficient. For an example, if a dilution of 1:1500 of the test solution gives the same "kill" as 1:100 solution of phenol, the test sample has an RW of 15.

Phenolics have bactericidal and fungicidal properties and their strength tends to increase as their chain length increases. For example phenol has an RW coefficient of 1, M-Cresol has an RW coefficient of 2.3 and 2,6-xylenol has an RW coefficient of 3.8. Merisol XHBTA contains the heavier phenolics and has been tested to have RW coefficients of between 14.1 and 15.7. XHBTA contains approximately 15% 2,4/2,5-xylenol, 55% of the heavier xylenols and ethyl phenols, 25% high boiling point tar acid and 5% of pitch. It also acts as a hydrophobic agent and other coal tar derivatives with a higher pitch percentage can usefully be blended with this material.

What is claimed is:

1. A composition for impregnation of a lignocellulosic material, the composition comprising:
   (a) either
      (i) a high boiling point tar acid derived from a water stream produced during the distillation classification of coal; or
      (ii) a pitch derived from a water stream produced during the distillation classification of coal;
   (b) a solvent for component (a) selected from the group consisting of a low carbon alcohol selected from the group consisting of methanol, ethanol, propanol and butanol, an azeotrope of the low carbon alcohol and another solvent, and a mixture of the low carbon alcohol and water;
   (c) a resin component consisting essentially of phenol formaldehyde resole resin;

(d) optionally an acid catalyst for the phenol formaldehyde resole resin; and (e) optionally a formaldehyde donor or a precursor of formaldehyde.

2. A composition according to claim 1 comprising:

(a) the high boiling point tar acid or the pitch in an amount of from 2% to 60% inclusive by mass of the combined mass of components (a), (b) and (c);

(b) the solvent is an amount of from 50% to 97% inclusive by mass of the combined mass of components (a), (b) and (c);

(c) the phenol formaldehyde resole resin in an amount of from 1% to 30% inclusive by mass of the combined mass of components (a), (b) and (c);

(d) the acid catalyst in an amount of from 1% to 15% by mass of the resin; and (e) the formaldehyde donor or the precursor of formaldehyde in an amount of from 1% to 15% inclusive by mass of the mass of the high boiling point tar acid or the pitch.

3. A composition according to claim 2 comprising the high boiling point tar acid or the pitch in an amount of from 8% to 15% inclusive by mass of the combined mass of components (a), (b) and (c).

4. A composition according to claim 2 or claim 3 comprising the solvent in an amount of from 77% to 90% inclusive by mass of the combined mass of components (a), (b) and (c).

5. A composition according to claim 2 comprising the phenol formaldehyde resole resin in an amount of from 2% to 8% inclusive by mass of the combined mass of components (a), (b) and (c).

6. A composition according to claim 2 comprising the acid catalyst in an amount of from 4% to 6% inclusive by mass of the resin.

7. A composition according to claim 2 comprising the formaldehyde donor or the precursor of formaldehyde in an amount of from 8% to 12% inclusive by mass of the mass of the high boiling point tar acid or the pitch.

8. A composition according to claim 1 wherein the solvent is selected from a group consisting of methanol, an aceotrope of methanol and another solvent, and a mixture of methanol and water.

9. A composition according to claim 1 wherein the formaldehyde donor or the precursor of formaldehyde is selected from the group consisting of hexamethylene tetramine, methylene glycol, trimethylene glycol, and paraformaldehyde.

10. A method of preparing a finished product from a lignocellulosic material, including the steps of:

(1) impregnating the lignocellulosic material with an impregnating composition comprising:

(a) either
 (i) a high boiling point tar acid derived from a water stream produced during the distillation classification of coal; or
 (ii) a pitch derived from a water stream produced during the distillation classification of coal;

(b) said component (a) being partially or completely dissolved in a solvent therefor selected from the group consisting of a low carbon alcohol selected from the group consisting of methanol, ethanol, propanol and butanol, an azeotrope of the low carbon alcohol and another solvent, and a mixture of the low carbon alcohol and water;

(c) a resin component consisting essentially of a phenol formaldehyde resole resin;

(d) optionally an acid catalyst for the phenol formaldehyde resole resin; and (e) optionally a formaldehyde donor or a precursor of formaldehyde;

(2) removing the solvent from the product of step (1), optionally with recovery thereof for re-use; and (3) subjecting the product of step (2) to suitable conditions of temperature and optionally of pressure to polymerise or to set the resin, to form the finished product.

11. A method according to claim 10 wherein step (1) is carried out by immersing the lignocellulosic material in the impregnating composition or by impregnating the lignocellulosic material with the impregnating composition under suitable conditions of vacuum and pressure.

12. A method according to claim 10 or claim 11 wherein in step (3) the product of step (2) is subjected to an elevated temperature to allow the resin to polymerise or to set.

13. A method according to claim 10 or claim 11 wherein in step (3) the product of step (2) is subjected to an elevated temperature and pressure to allow the resin to polymerise or to set.

14. A method according to claim 10 wherein the impregnating composition comprises:

(a) the high boiling point tar acid or the pitch in an amount of from 2% to 60% inclusive by mass of the combined mass of components (a), (b) or (c);

(b) the solvent in an amount of from 50% to 97% inclusive by mass of the combined mass of components (a), (b) and (c);

(c) the phenol formaldehyde resole resin in an amount of from 1% to 30% inclusive by mass of the combined mass of components (a), (b) and (c);

(d) the acid catalyst in an amount of from 1% to 15% by mass of the resin; and (e) the formaldehyde donor of the precursor of formaldehyde in an amount of from 1% to 15% inclusive by mass of the mass of the high boiling point tar acid or the pitch.

15. A method according to claim 14 wherein the impregnating composition comprises the high boiling point tar acid or the pitch in an amount of from 8% to 15% inclusive by mass of the combined mass of components (a), (b) and (c).

16. A method according to claim 14 wherein the impregnating composition comprises the solvent in an amount of from 77% to 90% inclusive by mass of the combined mass of components (a), (b) and (c).

17. A method according to claim 14 wherein the impregnating composition comprises the phenol formaldehyde resole resin in an amount of from 2% to 8% inclusive by mass of the combined mass of components (a), (b) and (c).

18. A method according to claim 14 wherein the impregnating composition comprises the acid catalyst in an amount of from 4% to 6% inclusive by mass of the resin.

19. A method according to claim 14 wherein the impregnating composition comprises the formaldehyde donor or the precursor of formaldehyde in an amount of from 8% to 12% inclusive by mass of the mass of the high boiling point tar acid or the pitch.

20. A method according to claim 10 wherein the solvent of the impregnating composition is selected from the group consisting of methanol, an azeotrope of methanol and another solvent, and a mixture of methanol and water.

21. A method according to claim 10 wherein the formaldehyde donor or the precursor of formaldehyde is selected from the group consisting of hexamethylene tetramine, methylene glycol, trimethylene glycol, and paraformaldehyde.

22. A finished product comprising a lignocellulosic material which has been impregnated with an impregnating composition comprising:
(a) either
   (i) a high boiling point tar acid derived from a water stream produced during the distillation classification of coal; or
   (ii) a pitch derived from a water stream produced during the distillation classification of coal;
(b) said component (a) being partially or completely dissolved in a solvent therefor selected from the group consisting of a low carbon alcohol selected from the group consisting of methanol, ethanol, propanol and butanol, an azeotrope of the low carbon alcohol and another solvent, and a mixture of the low carbon alcohol and water;
(c) a resin component consisting essentially of a phenol formaldehyde resole resin;
(d) optionally an acid catalyst for the phenol formaldehyde resole resin; and
(e) optionally a formaldehyde donor or a precursor of formaldehyde, the impregnated lignocellulosic material having been subjected to suitable conditions of temperature and optionally of pressure to polymerise or to set the resin, to form the finished product.

* * * * *